US006273134B1

(12) United States Patent
Edwards et al.

(10) Patent No.: US 6,273,134 B1
(45) Date of Patent: Aug. 14, 2001

(54) STERILIZER VALVE (75) Inventors: James R. Edwards, Dubuque; Francis J. Lahey, Durango; Kerry W. Leppert, Dubuque, all of IA (US)

(73) Assignee: Barnstead/Thermolyne Corporation, Dubugue, IA (US)

( * ) Notice: Subject to any disclaimer, the term of this patent is extended or adjusted under 35 U.S.C. 154(b) by 0 days.

(21) Appl. No.: 09/432,482

(22) Filed: Nov. 1, 1999

(51) Int. Cl.[7] ................................................. F16K 11/10
(52) U.S. Cl. ........................... 137/625.46; 422/242
(58) Field of Search .................. 137/625.46, 625.47; 422/242

(56) References Cited

U.S. PATENT DOCUMENTS

| | | | |
|---|---|---|---|
| 1,854,307 | * 4/1932 | Hapgood | 137/625.42 |
| 2,781,056 | 2/1957 | Carufel | 137/624 |
| 5,122,344 | * 6/1992 | Schmoegner | 422/111 |
| 6,158,467 | * 12/2000 | Loo | 137/625.47 |

* cited by examiner

*Primary Examiner*—John Fox
(74) *Attorney, Agent, or Firm*—Wood, Herron & Evans, L.L.P.

(57) ABSTRACT

A sterilizer valve including a valve body with an inlet, an outlet, a vent, and a centerbore intersecting the inlet, outlet and vent. The valve further includes a valve stem having a shot chamber for holding a volume of sterilizing fluid, a fill passage having one end in fluid communication with the shot chamber and a second end intersecting the exterior surface at a fill port. The valve stem also has fluid communicating paths extending through the interior and disposed in an external surface of the valve stem. The valve stem is rotatably disposed in the centerbore of the valve body to selectively fluidly connect the shot chamber with the vent through the fluid communication paths upon the valve stem having different rotational positions with respect to the valve body.

33 Claims, 10 Drawing Sheets

STERILIZER VALVE

FIELD OF THE INVENTION

The present invention relates to sterilizers and more particularly, to an improved sterilizer valve.

BACKGROUND OF THE INVENTION

Autoclaves for sterilizing instruments, for example, dental and surgical instruments, have been used for decades. Of particular interest are freestanding, self-contained autoclave units similar to that illustrated in FIG. 10. The prior art autoclave or sterilizer 20 includes a sterilizing chamber 22 surrounded by heaters, for example, band heaters (not shown). Upon placing the items to be sterilized in the chamber 22, a user, via a control panel (not shown), initiates a sterilizing cycle the first step of which is to use the heaters to heat the sterilizing chamber to a temperature, for example, 275° F. Upon reaching that temperature, the user is signaled to turn the knob 26 which operates a valve 28, sometimes referred to as a metering valve, thereby causing a known quantity of sterilizing fluid, for example, water or sterilizing chemicals, to flow from a shotwell 30 through tubing 32 into the chamber 22. The sterilizing fluid immediately vaporizes, thereby producing a sterilizing steam or vapor which creates a vapor pressure of 20–40 pounds per square inch.

Figure 10:
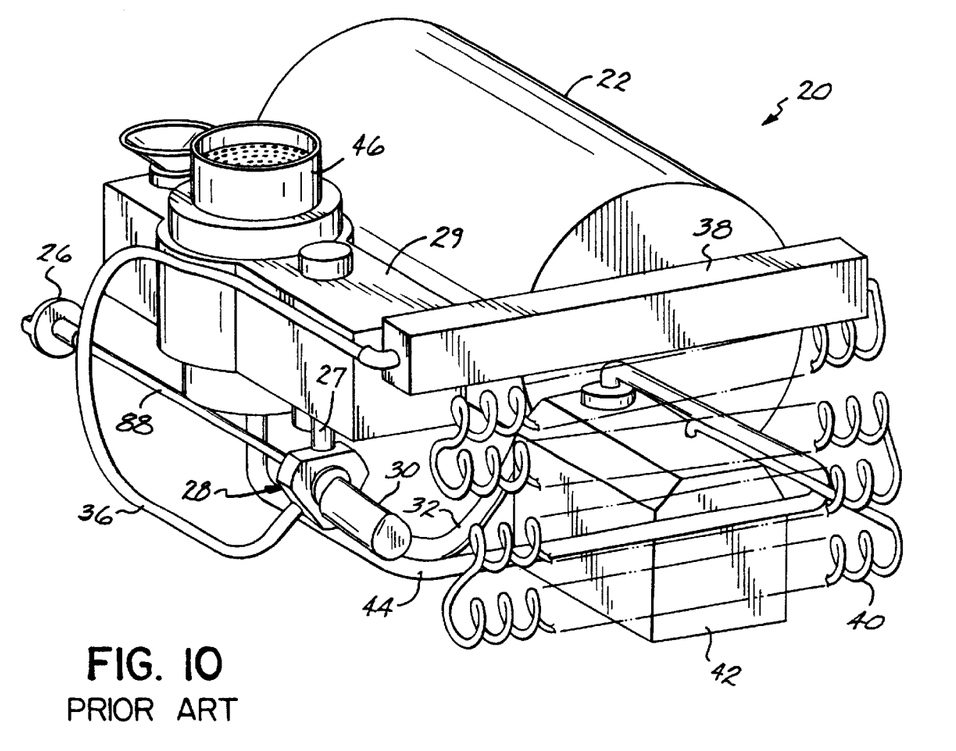
FIG. 10 is a schematic drawing of one embodiment of a known sterilizer with which the valve of the present invention may be utilized.

At the end of a sterilizing cycle, the operator is signaled to return the control knob 26 to its original position, and the valve 28 permits the sterilizing chamber 22 to be purged by a vacuum or pressurized air through a controlled vent system. Thus, the valve 28 functions as a two-way valve. The pressurized air is supplied to a purge inlet (not shown) of the sterilizing chamber 22 and forces the vapor from the sterilizing chamber 22, through the tubing 32, through the valve 28, through a vent line 36 and into a condensing manifold 38. The purged sterilizing vapors and fluid then pass through condensing and cooling coils 40 and into a waste tank 42. The waste tank is vented via tubing 44 through a carbon filter 46 to atmosphere. The manifold 38, coils 40, waste tank 40 and filter 46 function together to form a controlled vent system in which the used sterilizing fluid and vapors are contained and processed so that waste materials are collected and clean air is discharged into the environment. The specific structure of a controller vent system will vary depending on the sterilizer, the sterilizing fluid, the items being sterilized and other factors. A sterilizer providing the sterilizing cycle just described is commercially available as a Chemiclave EC5500/EC6000 from Barnstead|Thermolyne Corporation of Dubuque, Iowa.

Figure 11:
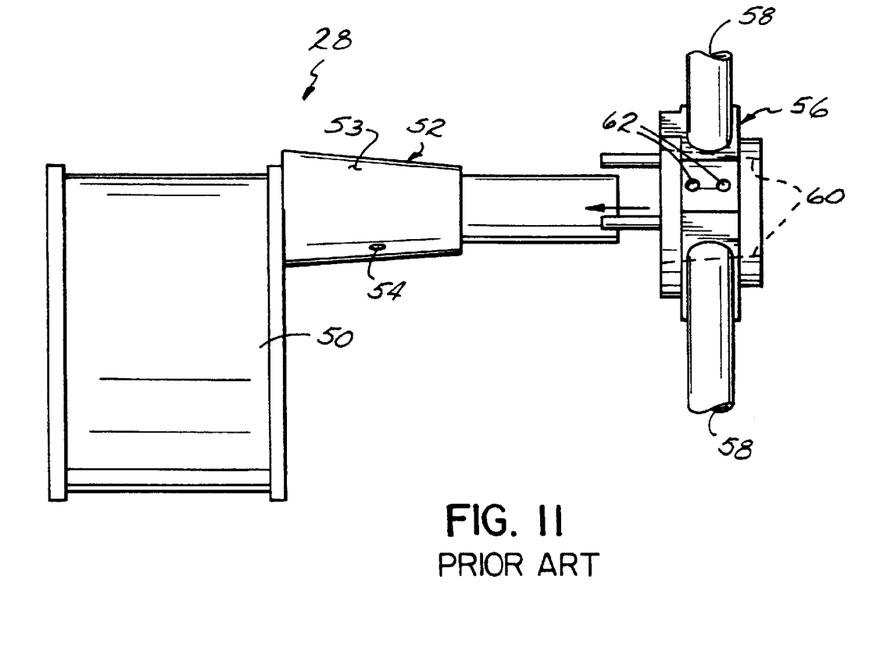
FIG. 11 is a partially disassembled view of one known valve.

Of interest to the present invention is one known valve 28 which is shown as partially disassembled in FIG. 11. The valve 28 has a shotwell 50 which is fluidly connected to a valve stem 52 that includes various passages 54 that are operatively coupled to passages within a valve body 56, thereby interconnecting ports 58 in the appropriate manner to achieve the desired two-way valving action. A valve of the construction shown in FIG. 11 has proven to have certain disadvantages. For example, the tapered sides 53 of the valve stem 52 must be machined to perfectly match the tapered sides 60 of a bore within the valve body 56. The mating of the tapered sides 53 with the tapered sides 60 must provide a tight seal against the fluids and pressurized vapors passing through the valve 28. Therefore, the tapered sides 53, 60 must have very accurate manufacturing tolerances so that such a seal is achieved. Further, the tapered sides 53 on the valve stem 52 are also coated with a "TEFLON" material which is machined to provide the final taper to the desired accuracy. The valve body 56 is normally nickel plated to provide the desired hardness. The processes of applying the "TEFLON" coating and nickel plating are expensive and if not properly performed, can contribute to a malfunction of the valve 28. The net result is that valves of such a design are difficult to manufacture and sometimes fail after a relatively short period of time.

The valve 28 provides only a single position of the valve body 56 with respect to the valve stem 52 at which the shotwell 50 is purged of any excessive pressurized sterilizing fluid and/or vapors. In that position, the vent holes 62 of the valve body 56 are aligned with the vent holes 54, thereby purging pressurized vapors from the shotwell 50 directly into the atmosphere and bypassing the controlled vent system within the sterilizer used to vent the chamber 22. With this valve construction, the shotwell is normally vented to atmosphere within the sterilizer housing. As will be appreciated, venting pressurized vapors within the sterilizer housing has several disadvantages. First, the vapors and fluid are hot and under pressure which results in such vapors and/or fluid being projected from the holes 62 into the housing of the sterilizer. Such spitting action of the sterilizing fluid and/or vapors is unpredictable. Not only is it undesirable to have an uncontained liquid within the sterilizer housing, but such vented vapors and liquid may present an undesirable odor, possibly facilitate corrosion and in some applications be volatile.

Figure 12:
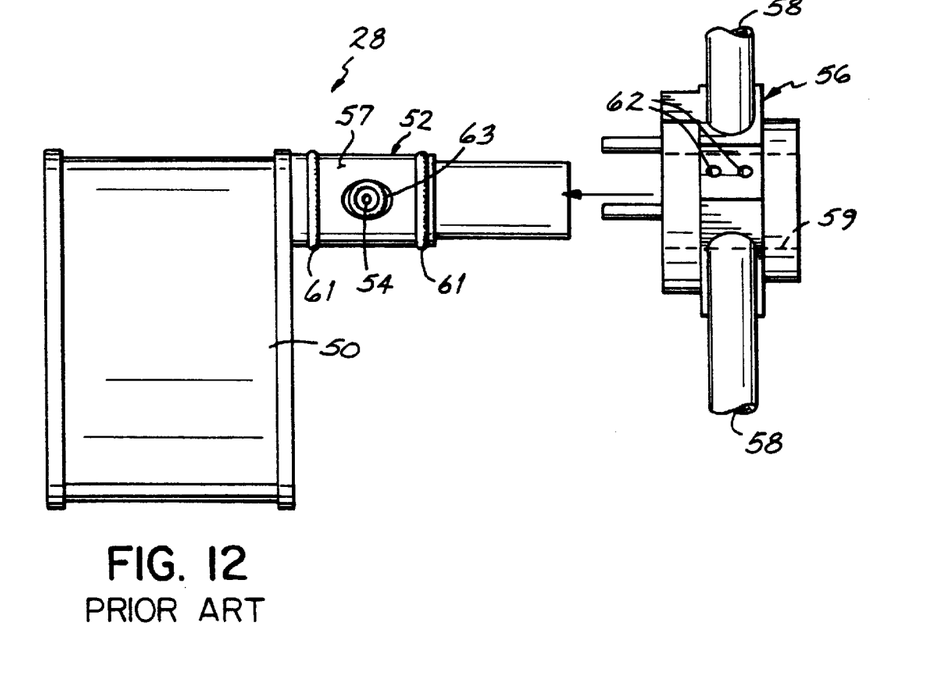
FIG. 12 is a partially disassembled view of another known valve.

Another known valve 28 is shown partially disassembled in FIG. 12. Valve components in FIG. 12 that are common with those described earlier with respect to FIG. 11 are commonly numbered. The valve stem 52 has a straight cylindrical side 57, and slides into a cylindrical bore 59 within the valve body 56. O-rings 61 are used to seal the valve stem 52 within the cylindrical bore 59, and an O-ring 63 is used to seal the fluid connection between each of the passages 54 within the valve stem and passages (not shown) intersecting the bore 59 within the valve body 56. While this design eliminates the problems associated with the tapered design of FIG. 11, the design of FIG. 12 is not trouble-free. The O-rings 63 often swell from their contact with the fluid and steam within the sterilizer, thereby making the valve stem difficult to turn by hand. Further, during rotation of the valve stem 52 within the valve body 56, as one of the compressed O-rings 63 passes over a leading edge of the passage openings within the bore 59 of the valve body 56, a portion of that O-ring 63 expands slightly into the valve body passage openings. Upon further rotation of the valve stem 52, that expanded portion of the O-ring 63 must pass over the trailing edge of the valve body passage opening and recompress. That action causes severe wear on the O-ring 63; and over time, the useful life of the O-ring 63 is significantly shortened. The valve 28 illustrated in FIG. 12 vents the shotwell 50 through holes 62, and thus, has the same disadvantages in that regard as previously discussed with respect to the valve illustrated in FIG. 11.

Figure 13:
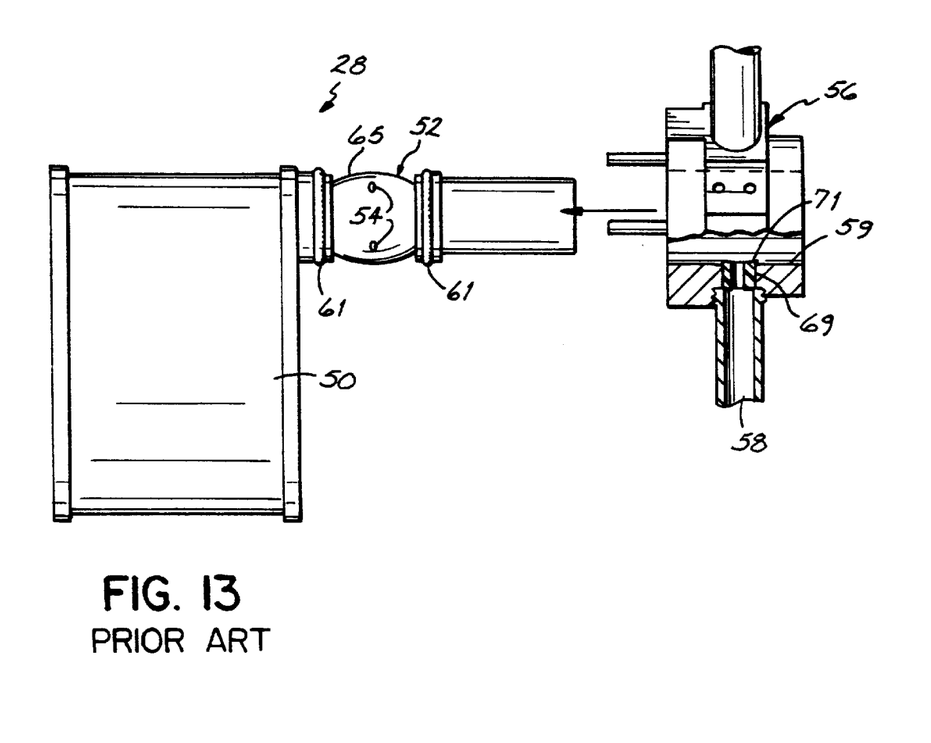
FIG. 13 is a partially disassembled view of a further known valve.

A further known valve 28 is shown partially disassembled in FIG. 13. Valve components in FIG. 13 that are common with those described above with respect to FIGS. 11 and 12 are commonly numbered. The valve stem 52 has a curved surface 65, and slides into a cylindrical bore 59 within the valve body 56. O-rings 61 are used to seal the valve stem 52 within the cylindrical bore 59. An annular rubber seal 69 extends through a sidewall of the valve body 56, and has a curved end 71 that matches the curve of the surface 65. The sterilizer valve illustrated in FIG. 13 has essentially the same problems as the sterilizer valve illustrated in FIG. 12.

Thus, there is a need for a sterilizer having an improved valve that provides more reliable long term operation.

SUMMARY OF THE INVENTION

The present invention provides an improved valve for a sterilizer that functions more reliably and has a longer life than prior valves. The valve of the present invention is more reliably manufactured with substantially fewer parts that must be reworked and/or scrapped than valves of prior designs. Further, the valve of the present invention continuously vents sterilizing fluid and vapors from the shot chamber during rotation of the valve from its sterilize or pressurize to its depressurize positions. In addition, the venting of the shot chamber is vented through a controlled vent system, thereby preventing raw sterilizing fluids and vapors from escaping into the interior of the sterilizer housing and then into the environment. Thus, the valve of the present invention has the advantage of continuously venting the valve body whenever the valve is not in the sterilize or pressurize position. Further, venting the shot chamber and the valve through a controlled vent system instead of the interior of the sterilizer housing provides less wear and tear to the housing and other components of the sterilizer. In addition, such a shot chamber and valve venting is more environmentally and user friendly. The design of the valve of the present invention provides further advantages of being more efficiently and reliably manufactured as well as operating more reliably over a long life when compared to past valve designs.

In accordance with the principles of the present invention and the described embodiments, the invention provides a valve for a sterilizer having a valve body with an inlet, an outlet, a vent, and a centerbore intersecting the inlet, outlet and vent. The valve further includes a valve stem having a shot chamber for holding a volume of sterilizing fluid, a fill passage having one end in fluid communication with the shot chamber and a second end intersecting the exterior surface at a fill port. A fluid communication path extends through a vent channel disposed in an exterior surface of the valve stem. The valve stem is rotatably disposed in the centerbore of the valve body to selectively fluidly connect the shot chamber with the vent through the fluid communication path upon the valve stem having different rotational positions with respect to the valve body.

In one aspect of the invention, the fluid communication path is a vent passage extending through the valve stem.

In another embodiment, the invention provides a method of operating a sterilizer in which after preheating a sterilizing chamber containing items to be sterilized, a valve is moved from a first position to a second position to transfer a sterilizing fluid from the shot chamber to the sterilizing chamber, whereby the sterilizing fluid is converted to a sterilizing vapor under pressure that fills the sterilizing chamber, the shot chamber and all interconnecting passages while sterilizing the items in the chamber. Thereafter, the valve is returned to the first position, and a fluid communication path is provided from the shot chamber to a vent on the valve body during a substantial portion of travel in returning the valve to the first position, thereby venting the sterilizing vapor under pressure from the shot chamber through the vent in the valve body and a controlled vent system connected thereto.

In a further embodiment, the invention provides a sterilizer valve including a valve body with an inlet, an outlet, a vent and a centerbore intersecting the inlet, outlet and vent. The valve has a valve stem with a shot chamber for holding a volume of sterilizing fluid which is rotatably disposed in the centerbore of the valve body to selectively align the valve stem with the inlet, outlet and vent upon rotation of the valve stem with respect to the valve body. The valve body further includes a port seal disposed in each of the inlet, the outlet and the vent of the valve body, wherein the port seals have respective annular end surfaces biased toward and sealingly contacting an exterior surface of the valve stem body to prevent sterilizing fluid and vapors from passing between the annular end surfaces of the seals and the exterior surface of the valve stem body.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION OF THE INVENTION

Figure 1:
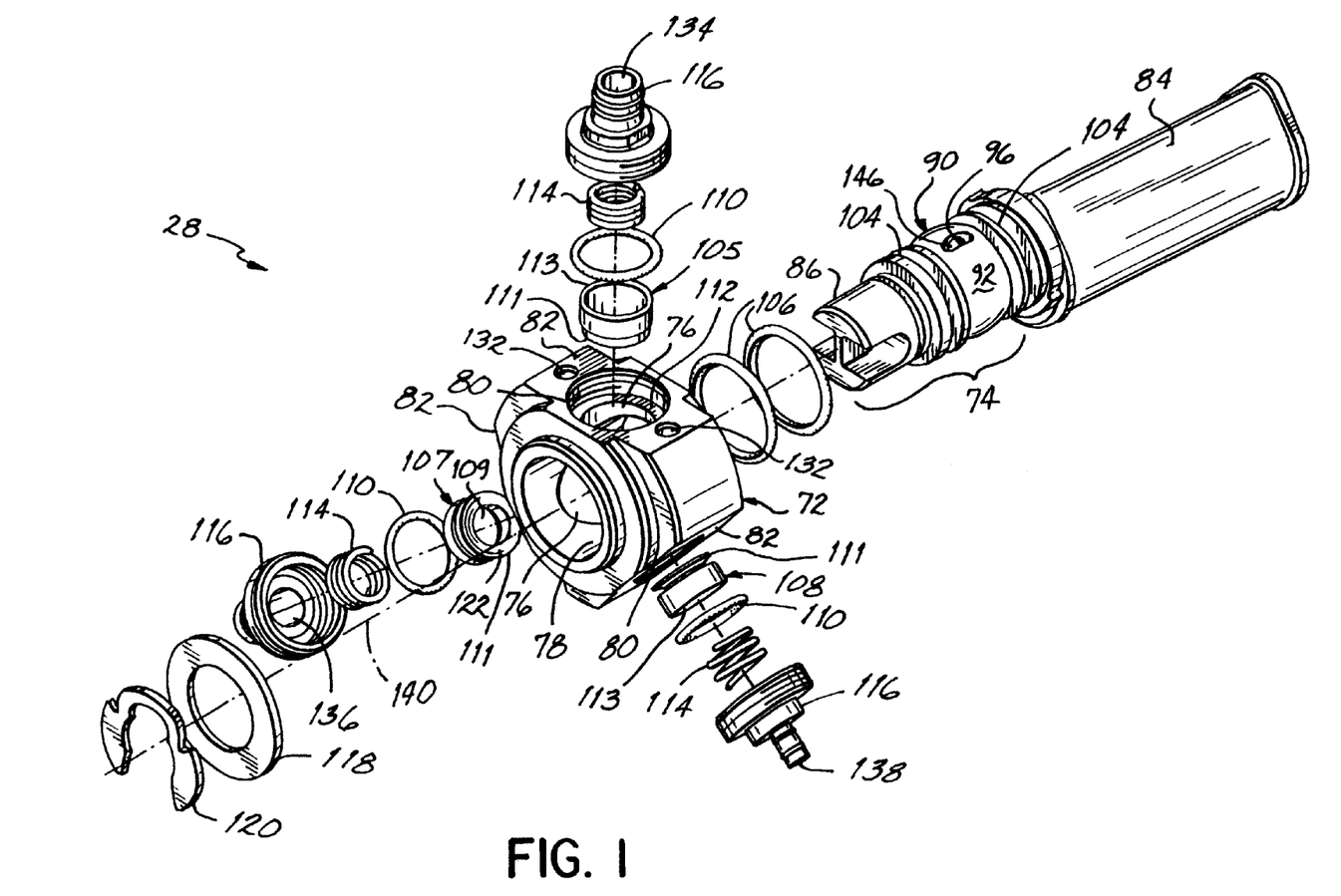
FIG. 1 is a disassembled perspective view of a valve for use with a sterilizer in accordance with the principles of the present invention.
Figure 4:
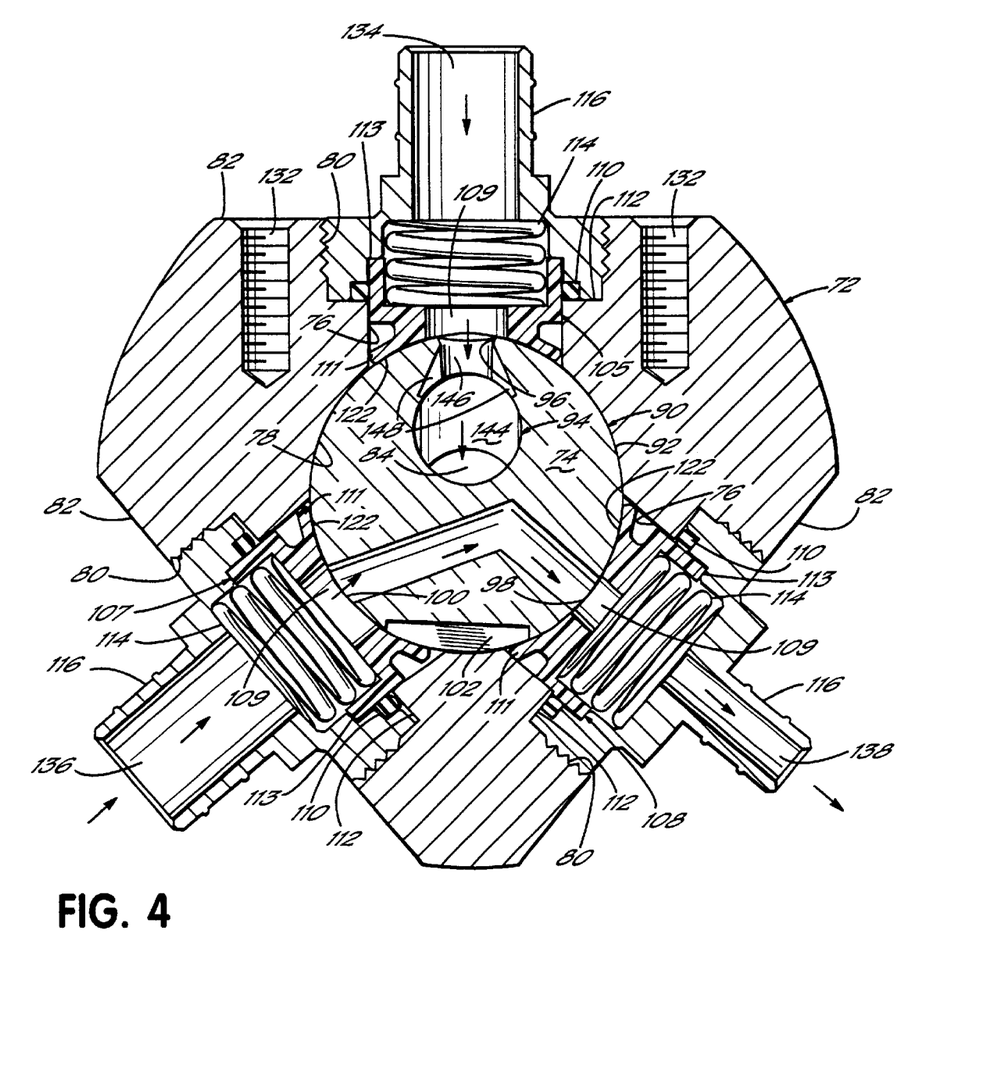
FIG. 4 is a cross-sectional view taken along line 4—4 of FIG. 2 and illustrates the depressurized position of the valve stem with respect to the valve body.

Referring to FIGS. 1 and 4, the valve 28 is comprised of a valve body 72 and a valve stem 74. The valve body 72 has three radially directed holes 76 that intersect a cylindrical center bore 78 extending axially through the valve body 72. Three threaded bores 80 are radially directed concentric with respective holes 76 and intersect three external surfaces 82 of the valve body 72.

The valve stem 74 has a shot chamber 84 connected to one end thereof. A coupling 86 is connected to the other end of the valve stem 74 and is shaped to drivingly engage one end of a control rod 88 (FIG. 10) the other end of which is connected to the control knob 26. Intermediate the shot chamber 84 and coupling 86 is a valve stem body 90. The valve stem body 90 has a curved, for example, spherical, surface 92 that is disposed within the valve body 72 adjacent the holes 76. The valve stem 74 includes a fill passage 94 that has one end in fluid communication with the shot chamber 84 and an opposite end in fluid communication with a fill port 96 located on the surface 92. The valve stem body 90 has a vent path or passage 97 extending therethrough and intersecting the surface 92 at one end to form a first vent port 98. The vent passage intersects the vent surface 92 at an opposite end to form a second vent port 100. The fill port 96 and vent ports 98, 100 are located on the major, that is, the largest, diameter of the valve curved surface 92. Further, the fill port 96 and vent ports 98, 100 are approximately equally spaced around the circumference of the major diameter of the valve stem body 90, thus being separated by approximately 120°. The three holes 76 within the valve body 72 are also equally angularly spaced and thus, separated by an angular displacement of approximately 120°. Another fluid path, for example, a vent channel or slot, 102 (FIG. 4) is formed in the exterior surface 92 of the valve stem body 90. The vent channel 102 forms a chord extending across the major diameter of the curved surface 92 and is approximately equally spaced between the vent ports 98, 100. The fill port 96, vent ports 98, 100 and channel 102 all intersect a common plane 103 that is substantially perpendicular to an axial, longitudinal centerline 140 of the valve stem 74. The centerline 140 is also an axis of rotation of the valve stem 74 within the valve body 72. Preferably, that common plane 103 is coincident with the major diameter of the curved surface 92.

The major diameter of the curved surface 92 is smaller, for example, by 0.010 inches, than the center bore 78 of the valve body 72. Thus, any sterilizing fluid or vapors exiting the shot chamber 84 through fill port 96 are free to flow between the curved surface 92 and the center bore 78 of the valve body. The valve stem 74 has two grooves 104 axially displaced from each other and located at opposite ends of the valve stem body 90. The two grooves 104 receive respective O-rings 106. The two O-rings 106 sealingly engage the center bore 78 of the valve body 72, thereby preventing any fluids or vapors from leaking along the stem 74 and out of the valve 28.

Each of the three holes 76 receives a respective seal 105, 107, 108 that is preferably made of PTFE "TEFLON" material. Each of the seals 105, 107, 108 has an annular sealing area on an end surface 122 of a flexible lip 111. The flexible lip 111 facilitates the seal conforming to any alignment imperfections in the curved surface 92 of valve stem 74. The flexible lips 111 have a clearance fit between the outer diameter of the lips 111 and the side walls of respective holes 76. Such a fit allows the lip to flex and be equally pressurized during the sterilization cycle. Fluids and vapors are sealed within the three holes 76 by three O-rings 110 which are disposed onto surfaces 112 that connect the holes 76 with the threaded openings 80. Three compression springs 114 are disposed on top of respective port seals 105, 107, 108 and are held in place by a respective port nipples 116. Each of the three port nipples 116 has a threaded exterior that engages one of the threaded openings 80.

The O-rings 106 are first mounted within the grooves 104 of the valve stem 74. The valve stem is then inserted within the valve body 72 and secured in place by a nylon washer 118 and a snap ring clip 120. Thereafter, each valve port is assembled by inserting the respective seal 105, 107, 108, O-ring 110, spring 114 and nipple 116. The compression springs 114 control the bias or sealing forces with which the annular sealing areas 122 of the port seals 105, 107, 108 are pushed against, and in sealing contact with, the curved surface 92 of the valve stem 74. By selectively tightening the nipples 116 to a torque, for example, 35 inch-pounds, the compression springs 114 are consistently compressed, thereby providing a desired bias or sealing force on the annular sealing areas 122 of the lips 111 of the port seals 105, 107, 108. The biasing force facilitates the flexible lips 111 in conforming to imperfections in the curved surface 92 of the valve stem 74.

After all of the ports in the valve body 72 have been assembled, the assembled valve is preferably placed into an oven heated to approximately 275° F. for a period of approximately 40 minutes. The heat plus the forces of the springs 114 causes the annular seal areas or surfaces 122 of the seals 105, 107, 108 to conform to the curved surface 92. That conformance provides the maximum area of contact between the seals 105, 107, 108 and surface 92 and hence, the best possible seal therebetween. It should be noted that the outer diameter of the spring coils 114 is only slightly smaller than the inner diameter of the outer cylindrical sections 113 of the seals 105, 107, 108. Thus, the springs 114 provide an internal physical support to prevent the outer cylindrical sections 113 from bending inward in response to forces directed toward the center of the seals 105, 107, 108. For example, as the nipples 116 are tightened and during the above described heating process and also during the life of the valve 28, the O-rings 110 will apply forces against the outer surfaces of the cylindrical sections 113 which are directed radially inward. Without the springs 114 supporting the cylindrical sections 133, they may deflect or deform inward which permits the O-rings 110 to likewise change configuration and shift inward. That may weaken the seal provide by the O-rings 110 and possibly permit fluid to leak around the O-rings 110. Thus, the springs 114 provide an inner support for the cylindrical sections 113 to hold the O-rings 110 in their desired configuration and position, thereby, maintaining the integrity of the O-ring seals.

The valve stem is thus rotatably mounted within the valve body 72, and as the various ports 96, 98, 100 are placed in juxtaposition with the openings 76, the seals 105, 107, 108 are effective to prohibit any fluids or vapors that are passing through the ports 96, 98, 100 and the openings 76 from leaking into the volume bounded by the O-rings 106, the valve stem curved surface 92 and the cylindrical center bore 78.

Figure 2:
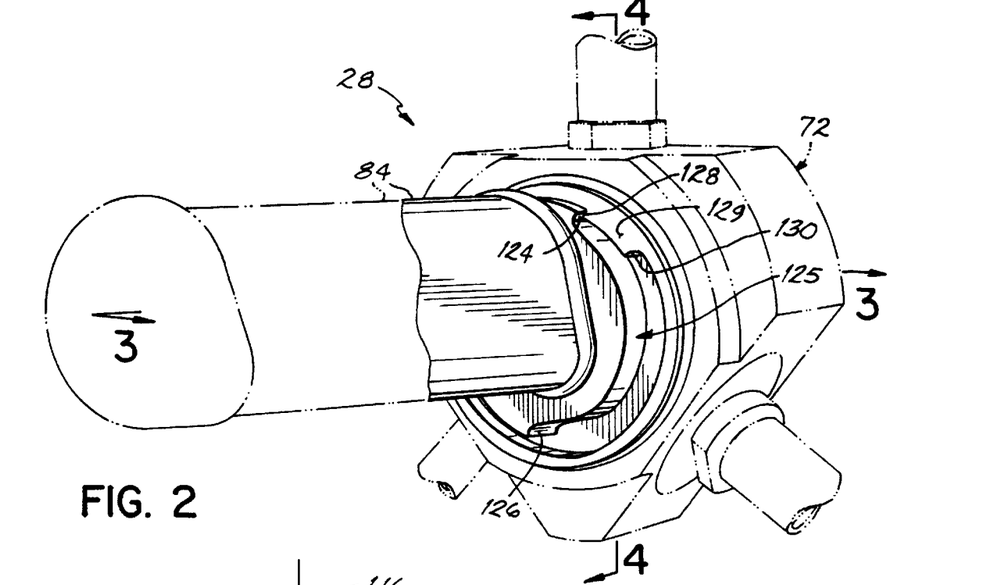
FIG. 2 is a perspective view of the assembled valve illustrated in FIG. 1.

Referring to FIG. 2, as previously described, the valve 28 has a first, pressurize position and a second, depressurize position. Those positions are determined by first and second stop surfaces 124, 126 on a stop member 125 located on the valve stem 74 between the valve body 90 and the shot chamber 84. The valve body has a stop member 129 extending outward from the valve body 72 in an axial direction toward the shot chamber 84 and in an interference relationship with the valve stem stop member 125. The valve body stop member 129 has first and second stop surfaces 128, 130 that are positioned to selectively engage the stop surfaces 124, 126 respectively. The valve body is secured to the sterilizer by fasteners (not shown) that extend into threaded mounting holes 132 (FIG. 1). Thus, turning the control knob 26 turns the valve stem 74 with respect to the fixed valve body 70. By turning the knob 26 (FIG. 10) in one direction, for example, clockwise, the stop surface 124 on the valve stem engages the stop surface 128 on the valve body 72 as shown in FIG. 2, thereby stopping the valve in the depressurize or fill position. By rotating the control knob 26 in the opposite direction, for example, counterclockwise, the stop surface 126 on the valve stem 74 engages the stop surface 130 on the valve body 72, thereby defining the pressurize position of the valve 28.

Referring to FIGS. 1 and 10, when mounted on the sterilizer, the inlet 134 of the valve 28 is connected via the inlet hose 27 to the reservoir tank 29 containing a supply of sterilizing fluid. The outlet 136 of the valve 28 is connected via an outlet tube 32 to the sterilizing chamber 22. A vent port 138 is connected via vent tubing 36 to a condensing manifold 38.

Figure 3:
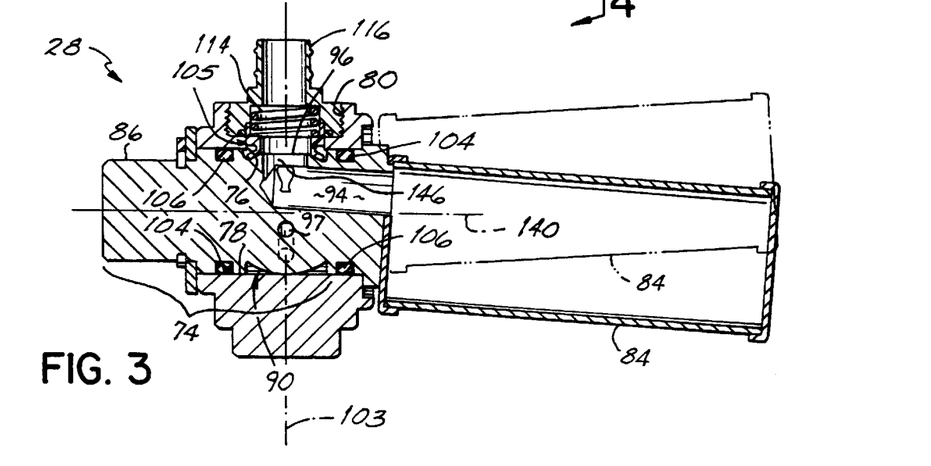
FIG. 3 is a centerline cross-sectional view of the valve taken along line 3—3 of FIG. 2.

In use, as shown in FIG. 4, the control knob 26 is initially in the depressurize or fill position. In this position, the valve inlet 134 is connected to the reservoir tank 29 (FIG. 10) via hose 27, thereby permitting sterilizing fluid to flow through a nipple 116, center hole 109 of a seal 108, the fill port 96, the fill passage 94 and into the shot chamber 84. As illustrated in FIG. 3, when in the depressurize position, the shot chamber 84 is tilted at a small angle, for example, 4°–4.5°, with respect to the longitudinal centerline 140 of the valve 28. When mounted on the sterilizer, the longitudinal centerline 140 is substantially horizontal. The slightly inclined position of the shot chamber 84 facilitates the filling of the chamber 84 as well as the fluid passage 96 interconnecting the chamber 84 with the reservoir 29 (FIG. 10). The depressurize or fill position is the default position for the valve 28; and thus, there is always substantial and sufficient time for the shot chamber 84 to fill with the sterilizing fluid. Upon the sterilizer achieving the desired temperature, the user is signaled, generally via an indicator light, to rotate the valve to the sterilize or pressurize position. The user rotates the control knob 26 approximately 120° counterclockwise to place the valve in the pressurize position.

Figure 5:
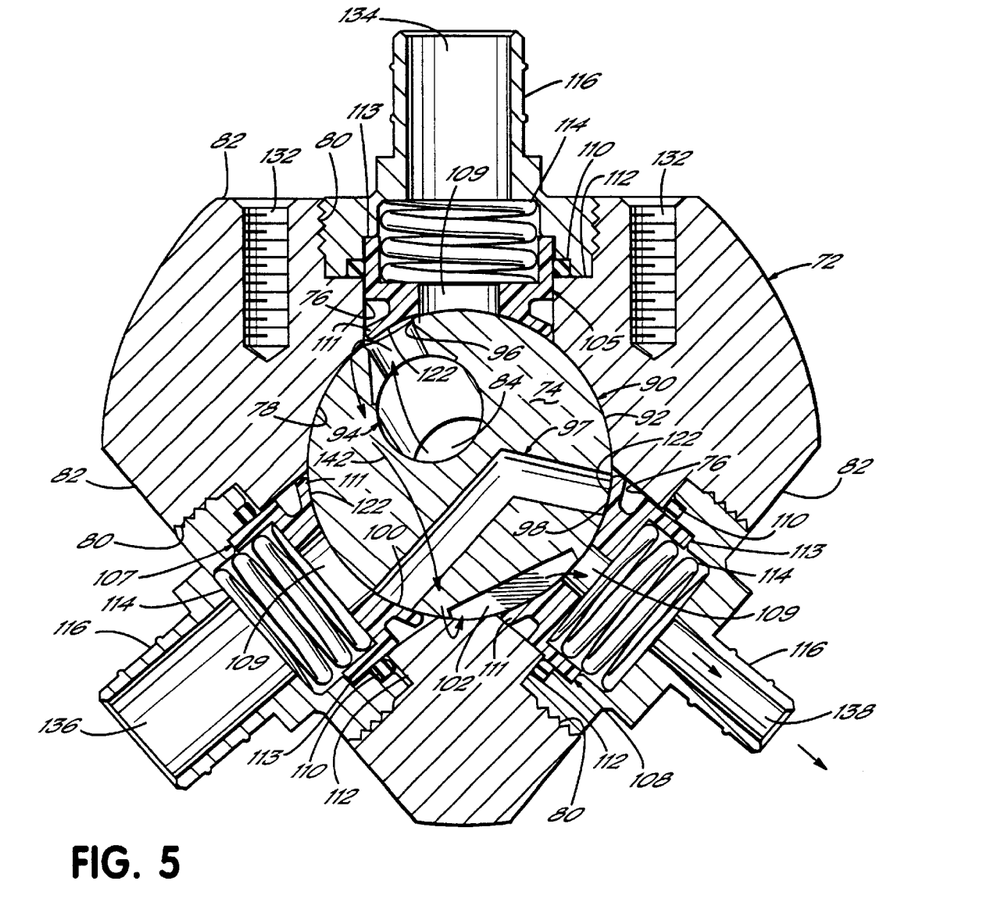
FIG. 5 is a cross-sectional view taken along line 4—4 of FIG. 2 and illustrates an upper vent position of the valve stem with respect to the valve body.
Figure 6:
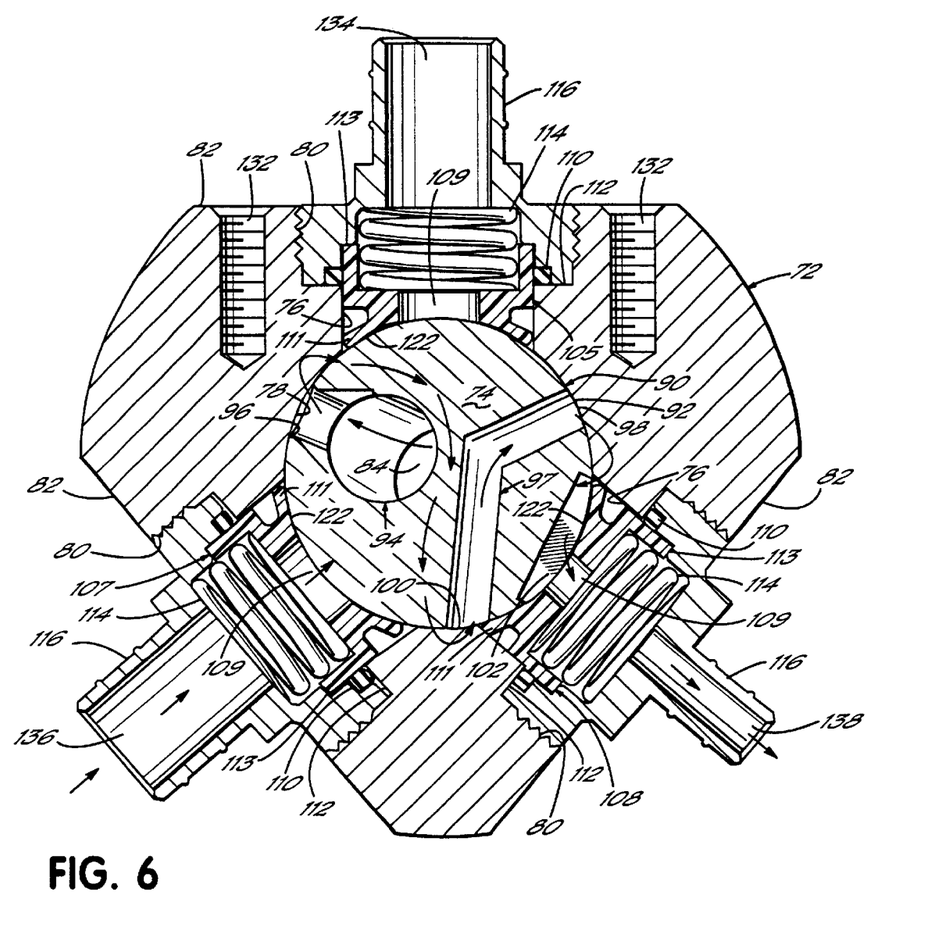
FIG. 6 is a cross-sectional view taken along line 4—4 of FIG. 2 and illustrates a non-venting position of the valve stem with respect to the valve body.
Figure 7:
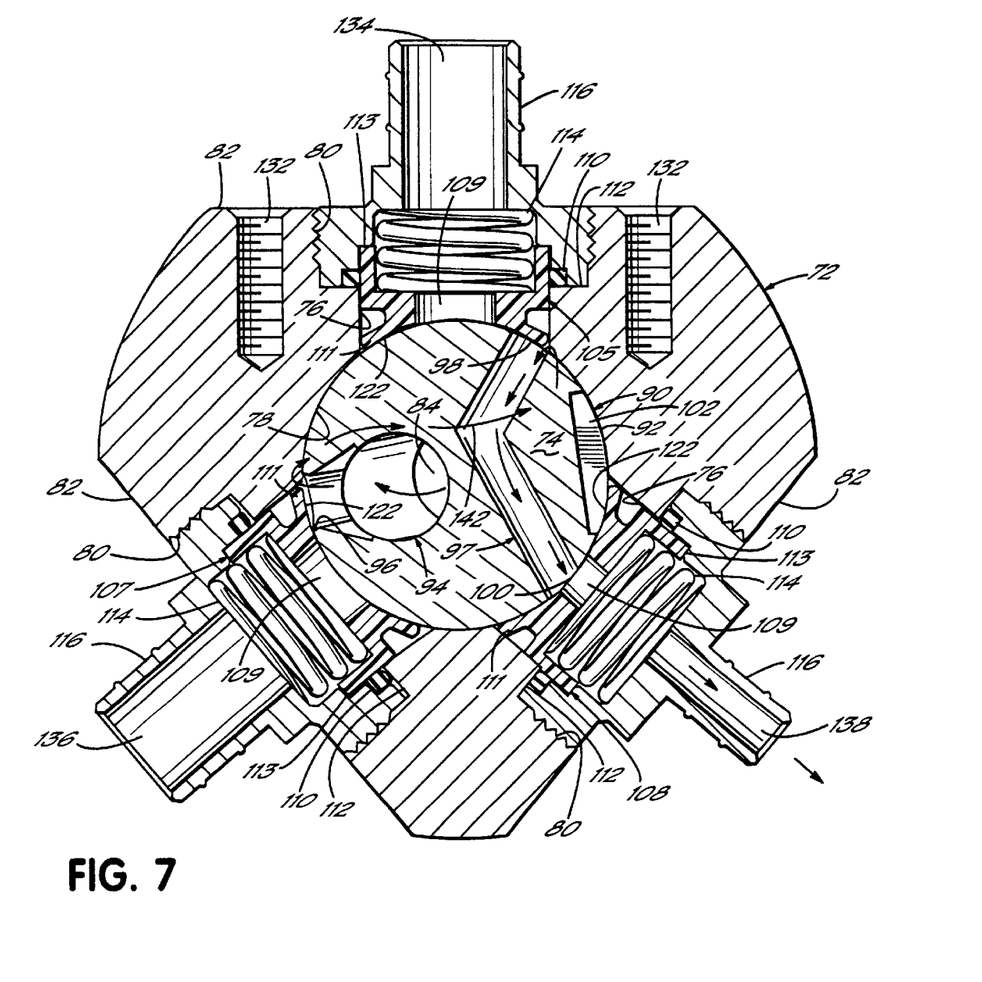
FIG. 7 is a cross-sectional view taken along line 4—4 of FIG. 2 and illustrates a lower vent position of the valve stem with respect to the valve body.

Referring to FIG. 5, as the fill port 96 is rotated past the annular seal area 122 of the seal 105 at the inlet 134, a small volume of sterilizing fluid is able to pass through the space between the valve stem surface 92 and the center bore 78 of the valve body 72 as shown by the flow arrows 142. That fluid exits the vent 138 of the valve by passing through the vent channel 102. Referring to FIG. 6, when the valve stem 74 is approximately halfway through its rotation to the pressurize position, a small quantity of sterilizing fluid can pass through the vent passage 97, through the vent channel 102 and out the vent 138. As shown in FIG. 7, fluid continues to pass through the vent 138 via the vent passage 97 until the fill port 96 is completely covered by the annular seal area 122 at the outlet 136.

Figure 8:
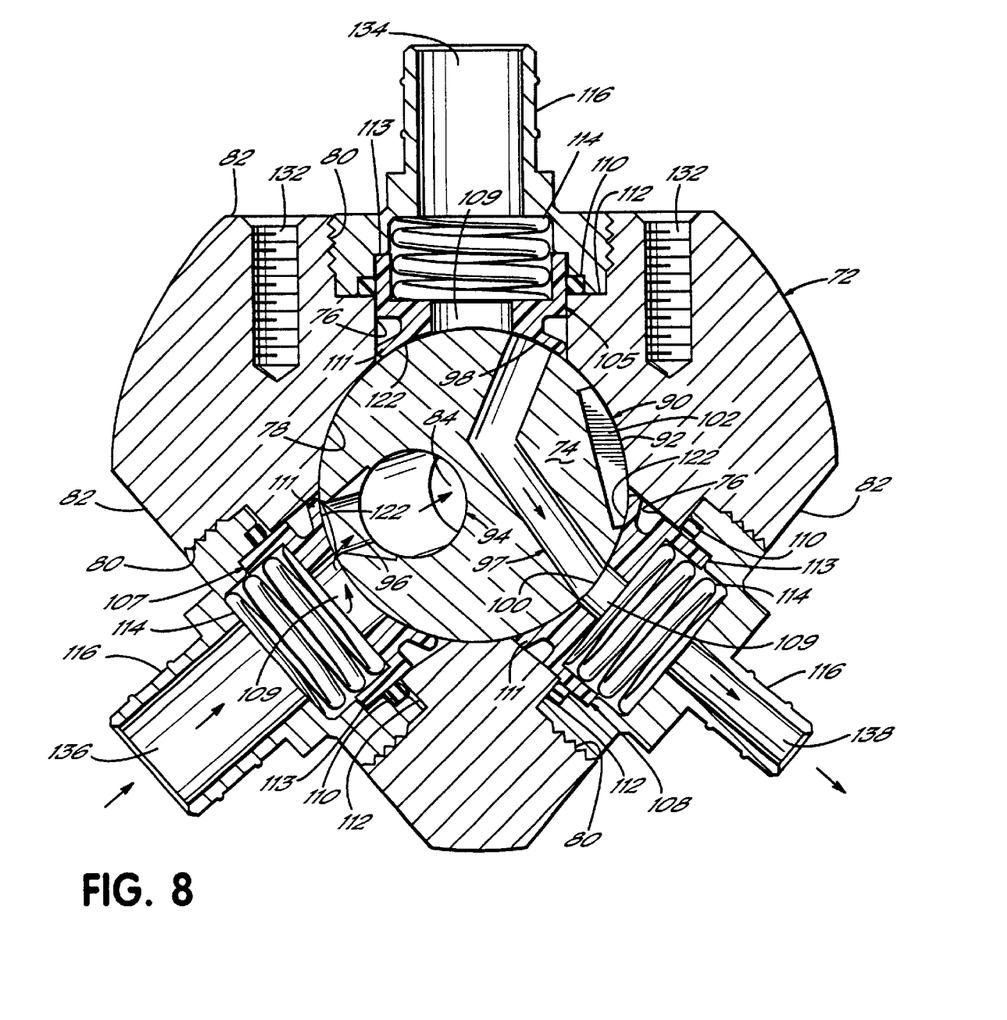
FIG. 8 is a cross-sectional view taken along line 4—4 of FIG. 2 and illustrates another non-venting position of the valve stem with respect to the valve body.
Figure 9:
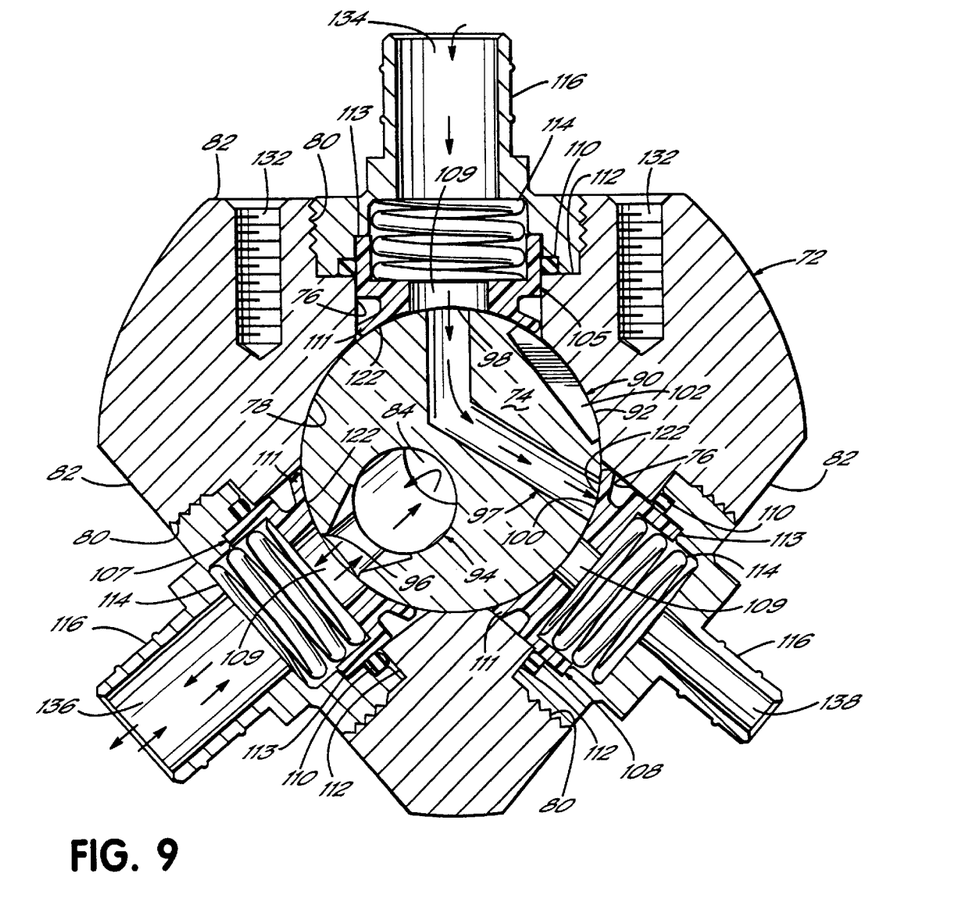
FIG. 9 is a cross-sectional view taken along line 4—4 of FIG. 2 and illustrates a pressurized position of the valve stem with respect to the valve body.

Referring to FIG. 8, as the valve stem 74 is rotated to a position where the fill port 96 opens to the center hole 109 of the seal 108 of the outlet 136, fluid from the shot chamber 84 drains from the shot chamber 84 through the fill passage 94, out the fill port 96, through the center hole 109 and through the outlet 136 into the sterilizing chamber 22. Referring to FIG. 9, when the valve 74 is turned fully to the pressurize position, the shot chamber 84 drains freely into the sterilizing chamber 22 through the outlet 136. As shown in FIG. 3, in phantom, when in the pressurize position, the shot chamber centerline is oriented approximately 4.25° above the horizontal to facilitate drainage of all of the sterilizing fluid into the sterilizing chamber 22. Upon entering the preheated sterilizing chamber 22, the sterilizing fluid vaporizes immediately, thereby creating a sterilizing vapor under pressure that fills the sterilizing chamber 22 as well as the shot chamber 84 and the intervening connecting passage 94. It should be noted that when in the pressurize position, the vent port 98 is connected to the reservoir 29, thereby filling the vent passage 97 with sterilizing fluid.

At the end of the sterilizing cycle, the operator, via a visual indicator, is advised that the sterilizing cycle is complete and that the valve 28 should be returned back to its depressurize position. Thus, the operator then manually rotates the knob 26 clockwise. Referring to FIG. 8, an initial clockwise rotation begins to seal the outlet 136 from the shotwell 84. However, the sterilizing fluid in the fill passage 97 freely drains out the vent 138. As the valve stem 74 is further rotated clockwise, the fill port 96 passes the outer edge of the annular sealing area 122 of the outlet 136, and the pressurized fluid and/or vapor within the shot chamber 84 and the fill passage 94 is free to relieve itself out of the fill port 96 into the space between the curved valve stem surface 92 and the center bore 78 of the valve body 72. That pressurized fluid and/or vapor as shown by the flow arrows 142, migrates around the exterior surface 92 of the valve stem 74 and into vent port 98 of vent passage 97. The pressurized fluid and/or vapor then exits through vent port 100 through the center hole 109 of seal 108 and out the vent 138.

Referring to FIG. 6, continued clockwise rotation of the valve stem 74 permits the shot chamber 84 to continue to vent through the vent passage 97 and the vent channel 102 and through the center hole 109 of the seal 108 and out the vent 138. As shown in FIG. 5, continued clockwise rotation of the valve stem 74 permits the shotwell 84 to vent through the vent channel 102 and out the vent 138. At this point in the rotation of the valve stem 74 to the depressurize position, the vent port 100 is beginning to open to the center hole of the seal 107 of the outlet 136 connected to the chamber 22 that contains pressurized sterilizing vapor. Referring to FIG. 4, when the valve stem 74 has been returned to its depressurize position, the sterilizing chamber 22 is connected via the outlet 136 and vent passage 97 to the vent 138 of the valve. Thus, a purge cycle of the sterilizer may be implemented to purge sterilizing vapors and fluid from the sterilizing chamber via outlet 136, vent passage 97 and vent 138 to the manifold 38 of FIG. 10. At the same time that the purge cycle is operational, sterilizing fluid is filling the shot chamber 84 for the next cycle via the reservoir 29, passage 27, inlet 134, hole 109 and passage 94.

The valve stem 74 has several improvements in its internal fluid passage design that facilitate a trouble free operation of the valve 28. Normally, with known valves, the fill passage 94 is comprised of an axial fluid path opening at one end into the shot chamber 84. The other end of the axial fluid path intersects a radial fluid path terminating at a fill port on the surface of the valve stem. Normally the radial fluid path and the fill port are respectively cylindrical and circular in shape. Further, often the diameter of the fill port is greater than the width of the edge of the seal. Thus, referring to FIG. 5, if the fill port 96 were large enough to straddle the seal lip 111, in returning the valve to the fill position after a sterilizing cycle, it is possible for the pressurized vapor to be released through the inlet 134 into the reservoir 29. Not only is it undesirable to have the reservoir tank 29 under pressure, but it is equally undesirable to permit vapors to escape via the reservoir tank 29 without being processed by a controlled vent system.

To eliminate the above disadvantages, the internal passages of the valve stem 74 has two improvements. Referring to FIG. 4, the internal fill passage 94 is comprised of a first fluid passage 144 that extends in a generally axial direction with respect to the valve stem and has one end intersecting the shot chamber 84. The other end of the first fluid passage 144 intersects an inner end of a second fluid passage 146 that extends in a generally radial direction with respect to the valve stem 74 and terminates with the fill port 96 at its outer end. Referring to FIG. 1, a first improvement to the valve stem 74 is that the second fluid passage 146 and the fill port 96 are noncircular in shape. The fill port 96 is narrower in a radial cross-section so that it does not straddle seal lips 111, but the second fluid passage 146 and the fill port 96 are elongated in the axial or longitudinal direction of the valve stem 74. Thus, the second fluid passage 146 and the fill port 96 have lengths in the axial direction with respect to the valve stem 74 that are greater than perpendicular widths of the respective second fluid passage 146 and fill port 96. The axially elongated second fluid passage 146 and fill port 96 provide for improved fluid flow therethrough.

Another potential flow problem can exist when the sterilizer has just finished its preheating cycle and is being used for the first time after some period of nonuse. First, the sterilizing fluid in the shot chamber 84 is often cooler, more viscous and has a greater resistance to flow. In addition, the preheat cycle can create a small residual pressure within the sterilizer, so that when the valve 28 is moved to the sterilize or pressurize position, there is a greater resistance to flow of the cooler fluid through the fill passage 94 and especially through the second fluid passage 146. To improve such flow, the valve stem 74 has a second improvement. Referring to FIG. 4, the side walls of the second fluid passage 146 have opposed slots 148 such that the second fluid passage 146 is narrowest at its outer end that intersect the fill port 96. As viewed with respect to a diametric cross-section of the valve stem 74 in FIG. 4, moving from the fill port 96 radially toward the centerline 140, the slots 148 flare outward to provide an increasing larger size of the second fluid passage 146. The slots flare out away from the length of the fill port 96 at an angle of approximately 25° with respect to a radius of the valve stem 74. With the slots 148, the second fluid passage is widest at its inner end which intersects with the first fluid passage 144. The slots have width in the axial direction of approximately 0.200 inches, but can range in width from less than 0.125 inches to over 0.200 inches. The slots 148 reduce the resistance to flow of the liquid as it is gravity fed from the shot chamber 84, through outlet 136 into the sterilizing chamber 22, thereby providing more reliable sterilizer operation immediately after a period of nonuse and with cooler reservoir fluid.

The sterilizer valve described herein is of a design that can be more reliably manufactured and functions more reliably to provide a longer life than prior valves. Further, with the sterilizer valve described herein, the shot chamber is vented through a controlled vent system, thereby preventing raw sterilizing fluids and vapors from escaping into the interior of the sterilizer housing and then into the environment. In addition, the shot chamber continuously vents sterilizing fluid and vapors from the shot chamber during rotation of the valve from its pressurize to its depressurize positions. Thus, the sterilizing valve of the present invention has the advantage of a maintenance free operating life that is more than twice prior valves and has the further advantage of providing less wear and tear to the housing and other components of the sterilizer as well as being more environmentally and user friendly.

While the present invention has been illustrated by a description of various embodiments, and while these embodiments have been described in considerable detail, it is not the intention of Applicants to restrict or in any way limit the scope of the appended claims to such detail. Additional advantages and modifications will readily appear to those skilled in the art. For example, a particular configuration of a vent passage 97 interior to the valve stem 74 and a vent channel 102 exterior to the valve stem 74 are shown and described. However, as will be appreciated, other configurations and combinations of interior and exterior vent passages and channels may be used to provide the advantage of a continuous venting of the shot chamber into a controlled vent system during a rotation of the valve stem 74. Such other configurations include a different configuration of only internal vent passages or only external vent channels. Further, the shape and size of the internal passages and external channel may be changed while achieving the advantages of the present invention.

The valve stem body is described as having a substantially spherical outer surface. Such a surface shape is preferred because a uniform sealing pressure is readily provided by the springs 114; however, as will be appreciated, external surfaces having other curved shapes upon which a desired seal can be made can also be used. For example, the curved surface can stretched slightly in the axial direction to form an ellipse having a major axis coincident with the centerline of the valve 28.

Thus, the invention in its broader aspects is not limited to the specific details, representative apparatus and method, and illustrative example shown and described. Accordingly, departures may be made from such details without departing from the spirit or scope of Applicants' general inventive concept.

What is claimed is:

1. A valve for a sterilizer comprising:
    a valve body having
        an inlet adapted to be connected to a reservoir of sterilizing fluid,
        an outlet adapted to be connected to a sterilizing chamber,
        a vent adapted to be connected to a vent system, and
        a centerbore intersecting the inlet, outlet and vent; and
    a valve stem having
        an exterior surface,
        a shot chamber for holding a volume of sterilizing fluid,
        a fill passage having one end in fluid communication with the shot chamber and a second end intersecting the exterior surface at a fill port, and
        a vent channel disposed in the exterior surface of the valve stem,
    the valve stem being rotatably disposed in the centerbore of the valve body to selectively fluidly connect the shot chamber with the vent through the vent channel upon the valve stem having different rotational positions with respect to the valve body.

2. A valve for a sterilizer of claim 1 further comprising a vent passage extending through the valve stem and having opposed vent ports intersecting the exterior surface, wherein the valve stem selectively fluidly connects the shot chamber with the vent through the vent channel and the vent passage upon the valve stem having different rotational positions with respect to the valve body.

3. A valve for a sterilizer of claim 1 wherein the vent channel forms a chord across the exterior surface of the valve stem.

4. A valve for a sterilizer of claim 2 wherein the vent channel extends across the exterior surface at a location approximately equally spaced between the vent ports.

5. A valve for a sterilizer of claim 1 wherein the fill port and the vent channel intersect a common plane substantially perpendicular to a longitudinal centerline of the valve stem.

6. A valve for a sterilizer of claim 2 wherein the external surface is a curved surface and the fill port, the vent channel and the vent ports intersect a common diametric plane of the external surface.

7. A valve for a sterilizer of claim 6 wherein the common diametric plane is coincident with a major diameter of the external surface.

8. A valve for a sterilizer of claim 2 wherein each of the inlet, the outlet and the vent has an annular seal area in contact with the exterior surface of the valve stem, and the vent channel and vent ports providing a continuous vent path between the shot well and the vent upon the fill port being outside an annular seal area of any of the seals.

9. A valve for a sterilizer comprising:
a valve body having
an inlet adapted to be connected to a reservoir of sterilizing fluid,
an outlet adapted to be connected to a sterilizing chamber,
a vent adapted to be connected to a vent system, and
a centerbore intersecting the inlet, outlet and vent;
a valve stem having
a valve stem body having an exterior surface, and
a shot chamber for holding a volume of sterilizing fluid,
the valve stem being rotatably disposed in the centerbore of the valve body to selectively align the valve stem with the inlet, outlet and vent upon rotation of the valve stem with respect to the valve body; and
a plurality of port seals, a port seal being disposed in the valve body at each of the inlet, the outlet and the vent and the port seals having respective annular end surfaces biased toward and sealingly contacting the exterior surface of the valve stem body to prevent sterilizing fluid and vapors from passing between the annular end surfaces of the seals and the exterior surface of the valve stem body.

10. A valve for a sterilizer of claim 9 wherein the exterior surface of the valve body is spherically shaped.

11. A valve for a sterilizer of claim 9 further comprising a fill passage having one end in fluid communication with the shot chamber and a second end intersecting a fill port on the exterior surface of the valve stem body.

12. A valve for a sterilizer of claim 10 further comprising a vent passage extending through the valve stem and intersecting vent ports on the exterior surface of the valve stem body.

13. A valve for a sterilizer of claim 9 further comprising a spring associated with each of seals to provide a biasing force against the exterior surface of the valve stem body.

14. A valve for a sterilizer of claim 9 wherein the seals are make of a PTFE "TEFLON" material.

15. A valve for a sterilizer comprising:
a valve body having
an inlet adapted to be connected to a reservoir of sterilizing fluid,
an outlet adapted to be connected to a sterilizing chamber,
a vent adapted to be connected to a vent system, and
a centerbore intersecting the inlet, outlet and vent;
a valve stem having
a valve stem body having an exterior surface, and
a shot chamber for holding a volume of sterilizing fluid,
the valve stem being rotatably disposed in the centerbore of the valve body to selectively align the valve stem with the inlet, outlet and vent upon rotation of the valve stem with respect to the valve body; and
a plurality of port seals, a port seal being extending through the valve body at each of the inlet, the outlet and the vent and the port seals having respective flexible lips with annular end surfaces sealingly contacting the exterior surface of the valve stem body to prevent sterilizing fluid and vapors from passing between the annular end surfaces of the seals and the exterior surface of the valve stem body.

16. A valve for a sterilizer of claim 15 wherein each of the port seals has the flexible lip on one end and a cylindrical section on an opposite end.

17. A valve for a sterilizer of claim 16 further comprising a biasing element extending into the cylindrical section.

18. A valve for a sterilizer of claim 17 wherein the biasing element is a compression spring.

19. A valve for a sterilizer of claim 18 wherein the compression spring has an external diameter slightly smaller than in inner diameter of the cylindrical section, whereby the compression spring provides a support for the cylindrical section.

20. A valve for a sterilizer of claim 19 wherein an O-ring is disposed around the cylindrical section to provide a fluid seal between the port seal and the valve body.

21. A valve for a sterilizer of claim 20 wherein a nipple is threaded into the valve body at each of the inlet, the outlet and the vent, the nipple pushing against an end of the compression spring and compressing the compression spring to provide a bias on the flexible lip of the port seal.

22. A valve for a sterilizer of claim 17 wherein the port seal is made of a PTFE "TEFLON" material.

23. A valve for a sterilizer comprising:
a valve body having
an inlet adapted to be connected to a reservoir of sterilizing fluid,
an outlet adapted to be connected to a sterilizing chamber,
a vent adapted to be connected to a vent system, and
a centerbore intersecting the inlet, outlet and vent, and
a stop member extending axially from the valve body and having first and second stop surfaces circumferentially located with respect to the centerbore; and
a valve stem having
a valve stem body,
a shot chamber located at one end of the valve stem body and holding a volume of sterilizing fluid, and
a stop member having first and second stop surfaces and located between the valve stem body and the shot chamber,
the valve stem being rotatably disposed in the centerbore of the valve body, wherein rotation of the valve stem in one direction is stopped by the first stop surfaces on the valve stem contacting the first stop surface on the valve body and rotation of the valve stem in an opposite direction is stopped by the second stop surface on the valve stem contacting the second stop surface on the valve body.

24. A valve for a sterilizer comprising:
a valve body having
an inlet adapted to be connected to a reservoir of sterilizing fluid,
an outlet adapted to be connected to a sterilizing chamber,
a vent adapted to be connected to a vent system, and
a centerbore intersecting the inlet, outlet and vent; and
a valve stem having
an exterior surface, a shot chamber for holding a volume of sterilizing fluid, a fill passage having one end in fluid communication with the shot chamber and a second end intersecting the exterior surface at a noncircular fill port, and the valve stem being rotatably disposed in the centerbore of the valve body.

25. A valve for a sterilizer of claim 24 wherein the noncircular fill port is elongated to have a length in an axial direction with respect to the valve stem greater than a perpendicular width of the fill port.

26. A valve for a sterilizer of claim 25 wherein the fill passage further comprises:

a first fluid passage having one end intersecting the shot chamber; and a second fluid passage intersecting the first fluid passage at an inner end and intersecting the fill port at an outer end, the second fluid passage being elongated to have a length in an axial direction with respect to the valve stem greater than a perpendicular width of the second fluid passage.

27. A valve for a sterilizer of claim 26 wherein first fluid passage extends in a generally axial direction with respect to the valve stem and the second fluid passage extends in a generally radial direction with respect to the valve stem.

28. A valve for a sterilizer of claim 26 wherein the second fluid passage includes a slot portion making the second fluid passage narrower at its outer end and wider at its inner end.

29. A valve for a sterilizer of claim 28 wherein the second fluid passage includes two opposed slot portions extending outward from opposite sides of the width of the fill port, the second fluid passage with the two slot portions being narrower at its outer end and wider at its inner end.

30. A valve for a sterilizer of claim 29 wherein in a diametric cross-section of the valve stem, the slot portions flare out away from the length of the second fluid passage.

31. A valve for a sterilizer of claim 30 wherein the slot portions flare out at an angle of approximately 25° with respect to a radius of the valve stem.

32. A valve for a sterilizer comprising:

a valve body having an inlet adapted to be connected to a reservoir of sterilizing fluid, an outlet adapted to be connected to a sterilizing chamber, a vent adapted to be connected to a vent system, and a centerbore intersecting the inlet, outlet and vent; and a valve stem having an exterior surface having a fill port, a shot chamber for holding a volume of sterilizing fluid, a first fluid passage having one end intersecting the shot chamber, and a second fluid passage intersecting the first fluid passage at an inner end and intersecting the fill port at an outer end, the second fluid passage including a slot portion making the second fluid passage narrower at its outer end and wider at its inner end; and the valve stem being rotatably disposed in the centerbore of the valve body.

33. A valve for a sterilizer of claim 32 wherein the second fluid passage includes two opposed slot portions, each slot portion extending outward from one side of a width of the fill port, the second fluid passage with the two slot portions being narrower at its outer end and wider at its inner end.

* * * * *